(12) United States Patent
Huang et al.

(10) Patent No.: US 7,955,366 B2
(45) Date of Patent: Jun. 7, 2011

(54) BIOSTIMULATIVE ILLUMINATION APPARATUS

(75) Inventors: Chin-Tien Huang, Pusin Township, Changhua County (TW); Kai-Shu Sung, Wurih Township, Taichung County (TW)

(73) Assignee: Kai-Shu Sung, Taichung (TW)

( * ) Notice: Subject to any disclaimer, the term of this patent is extended or adjusted under 35 U.S.C. 154(b) by 127 days.

(21) Appl. No.: 11/925,638

(22) Filed: Oct. 26, 2007

(65) Prior Publication Data

US 2009/0112294 A1    Apr. 30, 2009

(51) Int. Cl.
*A61N 5/06* (2006.01)
(52) U.S. Cl. .................................. 607/88; 606/3; 606/10
(58) Field of Classification Search ............ 606/3, 9–12; 607/88–95
See application file for complete search history.

(56) References Cited

U.S. PATENT DOCUMENTS

| 4,930,504 | A  | * | 6/1990  | Diamantopoulos et al. ..... 607/88 |
| 6,494,900 | B1 | * | 12/2002 | Salansky et al. ................. 607/89 |
| 6,663,659 | B2 | * | 12/2003 | McDaniel ........................ 607/88 |
| 6,860,896 | B2 | * | 3/2005  | Leber et al. ........................ 607/1 |
| 6,866,678 | B2 | * | 3/2005  | Shenderova et al. ............ 607/88 |

* cited by examiner

*Primary Examiner* — Ahmed M Farah
(74) *Attorney, Agent, or Firm* — Chun-Ming Shih

(57) ABSTRACT

A biostimulative illumination apparatus for treating patient tissues includes at least one light emitting diode which can generate at least one narrow-pulse focused wave band suitable to be used as low-power and non-parallel focused light beams for biostimulative illumination. The wave length of the focused light beam is from 600 nm to 850 nm, the energy density of the focused light beams is from 2 Joule/cm$^2$ to 16 Joule/cm$^2$ and the divergence angle of the light beams is lower than 16°. In addition, the invention also provides a biostimulative illumination treatment method.

27 Claims, 5 Drawing Sheets

BIOSTIMULATIVE ILLUMINATION APPARATUS

FIELD OF THE INVENTION

The invention relates to a biostimulative illumination apparatus for treating patient tissues, and relates to a biostimulative illumination treatment method.

DESCRIPTION OF THE RELATED ART

Biostimulative illumination with low-power light is known as a treatment method. In conventional biostimulative illumination therapy, it always uses a focused light beam with a single frequency and a single energy, which limits the effect of the biostimulative illumination. Therefore, only using a focused light beam with a single frequency and a single energy, the biostimulative illumination therapy cannot be fully used. Additional, the focused light beam has a big divergence angle, which makes the energy density of the focused light beam is small and resulting in that the biostimulative illumination effect is not good.

To solve the above problems, the inventor of the invention researches many biostimulative illumination apparatuses and methods and successfully designs a biostimulative illumination apparatus of the invention.

BRIEF SUMMARY

One object of the invention is to provide a biostimulative illumination apparatus for treating patient tissues. The biostimulative illumination apparatus includes at least one light emitting at least onewave banddiode, which can generate at least one narrow-pulse focused wave band suitable to be used as low-power and non-parallel focused light beams for biostimulative illumination. The wave length of the focused light beams is from 600 nm to 850 nm, the energy density of the focused light beams is from 2 Joule/$cm^2$ to 16 Joule/$cm^2$ and the divergence angle of the focused light beams is lower than 16° and preferred from 4° to 10°.

Another object of the invention is to provide a biostimulative illumination system for treating patient tissues. The biostimulative illumination apparatus includes at least one group of light emitting diode apparatus, a driver and a power source. The group of light emitting diode apparatus includes at least one light emitting diode which can generate at least one narrow-pulse focused wave bandwave band suitable to be used as low-power and non-parallel focused light beams for biostimulative illumination, wherein the wave length of the focused light beams is from 600 nm to 850 nm, the energy density of the focused light beams is from 2 Joule/$cm^2$ to 16 Joule/$cm^2$ and the divergence angle of the light beams is lower than 16°. The driver includes a voltage control circuit and a MCU. The power source is used for supplying power for the biostimulative illumination apparatus.

The biostimulative illumination system further comprises a key apparatus connected to the CPU, for inputting the desired data of light energy and frequency.

The biostimulative illumination system further comprises an over-current protection circuit for protecting the biostimulative illumination system and patients.

The biostimulative illumination system further comprises a pulse adjusting circuit for receiving pulse signal from the MCU and generating voltages to the light emitting diode.

In addition, the invention provides a biostimulative illumination treatment method. The method includes the following steps:

(a) providing at least one said light emitting diode apparatus, which can emitting a narrowpulse wave band focusing on a spectrum area of red light or near-infrared light, wherein the wavelength of the narrow-pulse wave band is from 600 nm to 850 nm.

(b) driving at least one light emitting diode apparatus to emit non-continuous and non-parallel focused light beams having a divergence angle lower than 16°.

(c) illuminating to the patient tissue by non-parallel focused light beams, whose energy density is from 2 Joule/$cm^2$ to 16 Joule/$cm^2$.

The invention has the following advantages:

Because the divergence angle of the light beam is lower than 16° and the energy density of the focused light beam is from 2 Joule/$cm^2$ to 16 Joule/$cm^2$ in the invention, the light beam has a good penetrability to tissues and can reduce the recovering time of the wound.

BRIEF DESCRIPTION OF THE DRAWINGS

These and other features and advantages of the various embodiments disclosed herein will be better understood with respect to the following description and drawings, in which like numbers refer to like parts throughout.

DETAILED DESCRIPTION

Figure 1:
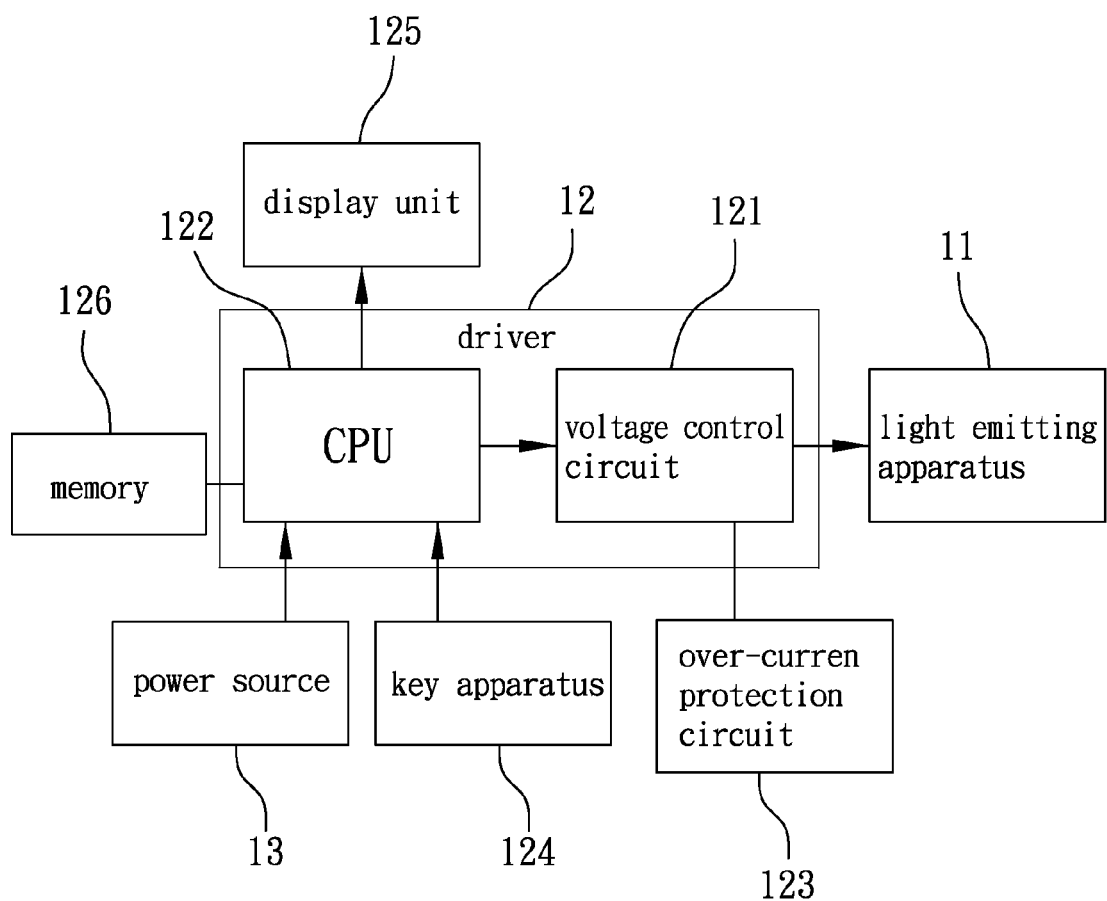
FIG. 1 is a schematic diagram of a biostimulative illumination apparatus of the invention.
Figure 2:
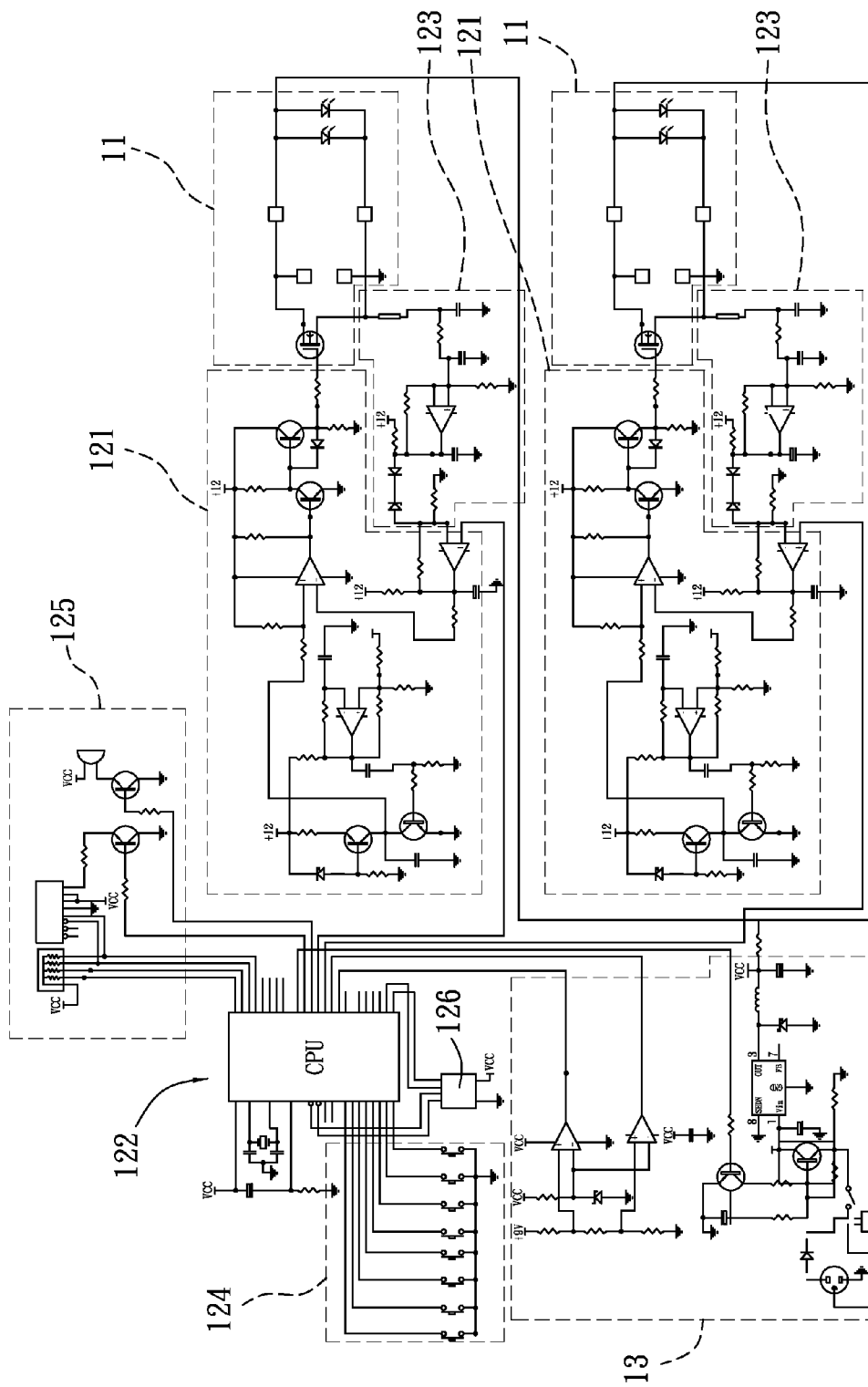
FIG. 2 is a detail circuit diagram of FIG. 1.

FIG. 1 is a schematic diagram of a biostimulative illumination apparatus of the invention. FIG. 2 is a detail circuit diagram of FIG. 1. The biostimulative illumination apparatus includes at least one group of light emitting diode apparatus 11, at least one driver 12 and a power source 13.

As shown in FIG. 1 and FIG. 2, the light emitting diode apparatus 11 includes at least one light emitting diode device such as a lacer diode (LD) or a light emitting diode (LED), which can emit at least one narrow-pulse focused wave band such as a spectrum area of red light or near-infrared light. The narrow-pulse focused wave band is suitable to be used as low-power and non-parallel focused light beams for biostimulative illumination. The wave length of the focused light beams is preferred from 600 nm to 850 nm. The energy density of the light beam is from 2 Joule/$cm^2$ to 16 Joule/$cm^2$ and preferred from 2.5 Joule/$cm^2$ to 5 Joule/$an^2$. The divergence angle of the focused light beams is from 4° to 10°. The light emitting diode apparatus 11 can be consisted of light emitting diodes with different wavelengths and be in some different wave bands to support some different usages.

As shown in FIG. 2, the biostimulative illumination apparatus includes two groups of the light emitting diode apparatuses 11. The biostimulative illumination apparatus also can include one group or more groups of the light emitting diode apparatuses 11.

As shown in FIG. 2, the driver 12 drives the light emitting diode apparatus 11 to generate a focused light. It includes a voltage control circuit 121 and a Central processing unit (CPU) 122. The voltage control unit 121 receives modulated pulses from the CPU 122 and then generates different output voltages to the light emitting diode apparatus 11 for generating focused lights with different energy. In the embodiment shown in FIG. 2, the voltage control circuit 121 is a pulse adjusting circuit. The CPU 122 computes the frequency of the focused light beam and provides a corresponding control signal to the voltage control circuit 121.

As show in FIG. 2, the power source 13 can be a power supply or a battery. To get a better power supplying, the power source 13 can be managed by some power management methods.

As shown in FIG. 1 and FIG. 2, the biostimulative illumination apparatus further includes a memory 126 connected with the CPU 122. The memory 126 is utilized for storing messages such as a treatment method, which can be referred in a next treatment.

As show in FIG. 1 and FIG. 2, the biostimulative illumination apparatus further includes over-current protection circuit 123 for protecting the voltage control circuit 123. The biostimulative illumination apparatus further includes a key apparatus 124 connected to the CPU 122 for inputting the desired voltage and frequency, which will be displayed on a display unit 125.

The biostimulative illumination treatment method of using the biostimulative illumination apparatus of the invention includes the following steps:

(a) providing at least one said light emitting diode apparatus, which can emitting a narrow-pulse wave band focusing on a spectrum area of red light or near-infrared light, wherein the wavelength of the narrow-pulse wave band is from 600 nm to 850 nm.

(b) driving at least one light emitting diode apparatus to emit a non-continuous and non-parallel focused light beam having a divergence angle from 0° to 16° (preferred from 4° to 10°).

(c) illuminating to the patient tissue by non-parallel focused light beams, whose energy density is from 2 Joule/$cm^2$ to 16 Joule/$cm^2$ and preferred from 2.5 Joule/$cm^2$ to 5 Joule/$cm^2$.

The biostimulative illumination apparatus includes six operation modes for treatment operation.

Figure 3:
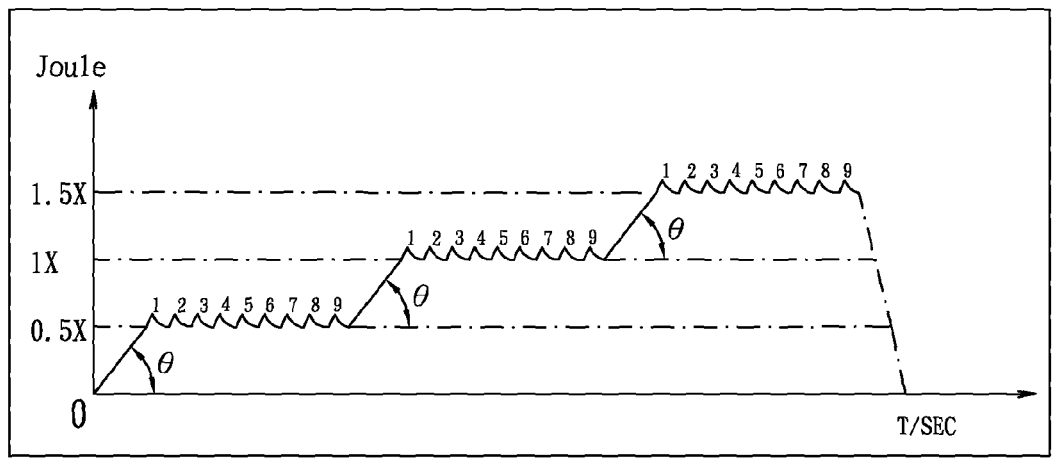
FIG. 3 is an energy curve diagram of the first mode of the biostimulative illumination apparatus.

FIG. 3 is an energy curve diagram of the first mode of the biostimulative illumination apparatus. The treatment method of the first mode includes three illumination steps with three different energies. In the three illumination steps, the light energies are from 2 Joule/$cm^2$ to 16 Joule/$cm^2$ and increases by 0.5X Joule, 1X Joule and 2X Joule, wherein X is a variable, and can be set by a doctor. The illumination energy increases by an angle $\theta$ ($\theta \leqq 60°$) after each step. The steps can be repeated many times. In the first mode, the energy of illumination light is lightly fluctuated at 6 times or 9 times and each time is from 0.5 second to 1.5 seconds. The fluctuating amplitude is lower than 20% and the fluctuating way is quickly ascending and slowly descending.

Figure 4:
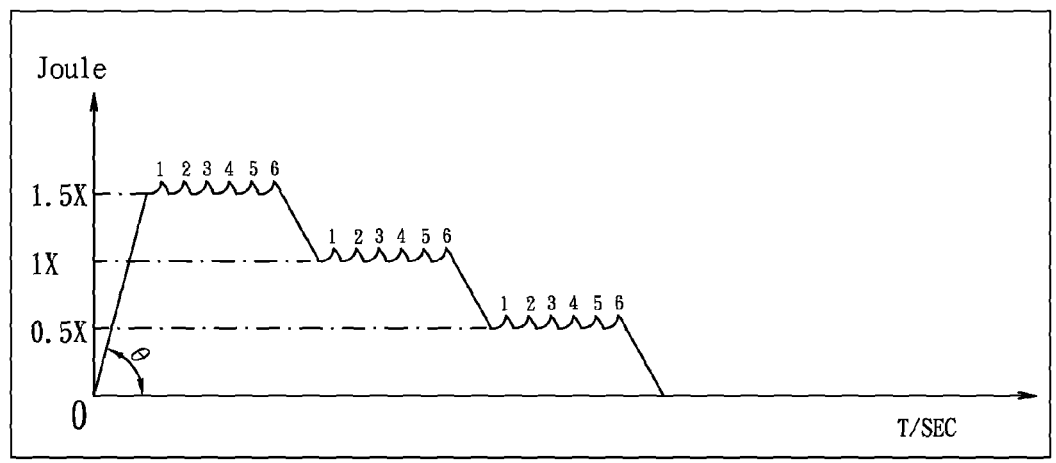
FIG. 4 is an energy curve diagram of the second mode of the biostimulative illumination apparatus.

FIG. 4 is an energy curve diagram of the second mode of the biostimulative illumination apparatus. The treatment method of the second mode includes three illumination steps with three different energies. In the three illumination steps, the light energies are from 2 Joule/$cm^2$ to 16 Joule/$cm^2$ and increases by 0.5X Joule, 1X Joule and 2X Joule, wherein X is a variable and set by a doctor, the illumination energy increases by an angle $\theta$ ($\theta \geqq 45°$) after each step. The steps can be repeated many times. In the second mode, the energy of illumination light is lightly fluctuated at 6 times or 9 times and each time is from 0.5 second to 1.5 seconds. The fluctuating amplitude is lower than 20% and the fluctuating way is slowly ascending and quickly descending.

Figure 5:
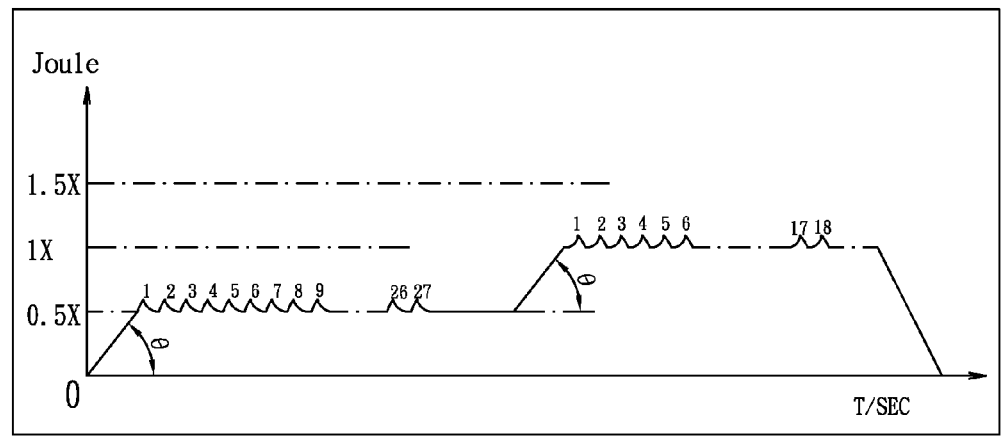
FIG. 5 is an energy curve diagram of the third mode of the biostimulative illumination apparatus.

FIG. 5 is an energy curve diagram of the third mode of the biostimulative illumination apparatus. The treatment method of the third mode includes two illumination steps with different energies. In the two illumination steps, the light energies are from 2 Joule/$cm^2$ to 16 Joule/$cm^2$ and increases by 0.5X Joule, 1X Joule and 2X Joule, wherein X is a variable and set by a doctor. The illumination energy increases by an angle $\theta$ ($\theta \leqq 60°$) after each step. The steps can be repeated many times. In the third mode, the energy of illumination light lightly fluctuates at many times and each time is from 0.5 second to 1.5 second. The fluctuating amplitude is lower than 20%. In the first step, the light fluctuates 9 or 27 times and the fluctuating way is quickly ascending and slowly descending. In the second step, the light fluctuates 6 or 18 times and the fluctuating way is slowly ascending and quickly descending.

Figure 6:
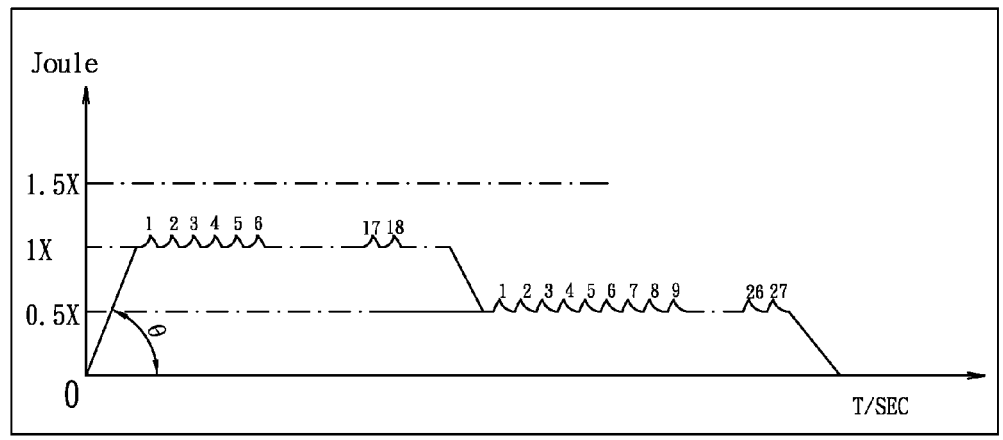
FIG. 6 is an energy curve diagram of the fourth mode of the biostimulative illumination apparatus.

FIG. 6 is an energy curve diagram of the fourth mode of the biostimulative illumination apparatus. The treatment method of the fourth mode includes two illumination steps with different energies. In the two illumination steps, the light energies are from 2 Joule/$cm^2$ to 16 Joule/$cm^2$ and increases by 0.5X Joule, 1X Joule and 2X Joule, wherein X is a variable. As set by a doctor, the illumination energy increases by an angle $\theta$ ($\theta \leqq 60°$) by each step. The steps can be repeated many times. In the fourth mode, the energy of illumination light lightly fluctuates at many times and each time is from 0.5 second to 1.5 seconds. The fluctuating amplitude is lower than 20%. In the fourth step, the light fluctuates 6 or 18 times and the fluctuating way is quickly ascending and slowly descending. In the second step, the light fluctuates 9 or 27 times and the fluctuating way is quickly ascending and slowly descending.

Figure 7:
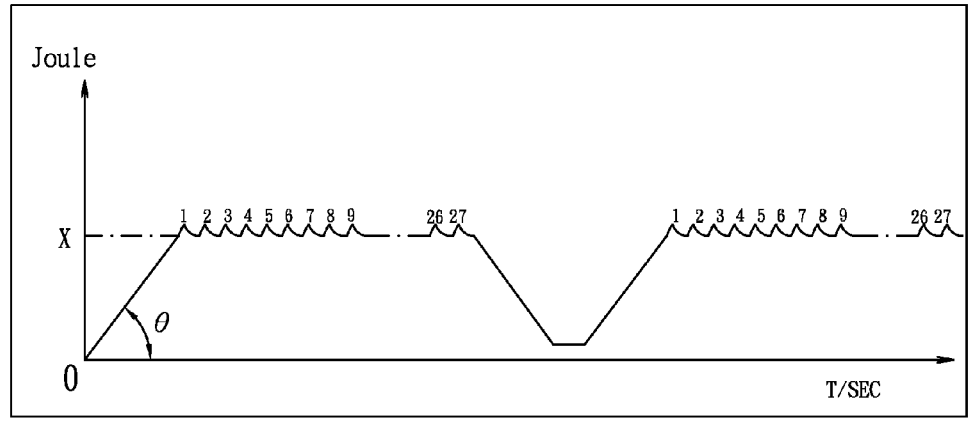
FIG. 7 is an energy curve diagram of the fifth mode of the biostimulative illumination apparatus.

FIG. 7 is an energy curve diagram of the fifth mode of the biostimulative illumination apparatus. The treatment method of the fifth mode includes an illumination step with a kind of light illumination energy. In the illumination step, the light energy is X Joule, wherein X is a variable and set by a doctor. The illumination energy increases by an angle $\theta$(about 45°). The step can be repeated many times. In the fifth mode, the energy of illumination light lightly fluctuates at 9 or 27 times and each time is between 0.5 to 1.5 second. The fluctuating amplitude is lower than 20%. The fluctuating way is quickly ascending and slowly descending.

Figure 8:
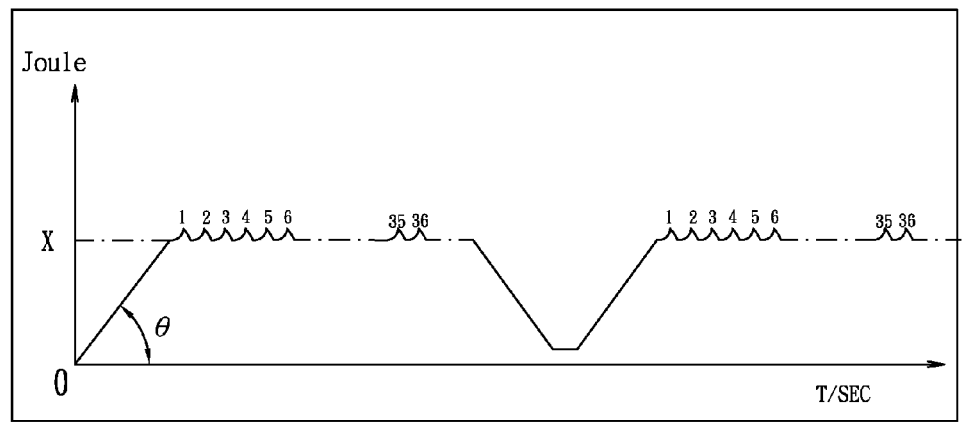
FIG. 8 is an energy curve diagram of the sixth mode of the biostimulative illumination apparatus.

FIG. 8 is an energy curve diagram of the sixth mode of the biostimulative illumination apparatus. The treatment method of the sixth mode includes an illumination step with a kind of light illumination energy. In the illumination step, the light energy is X Joule, wherein X is a variable and set by a doctor. The illumination energy increases by an angle $\theta$(the $\theta$ is approximately equal to 45°). The step can be repeated many times. In the fifth mode, the energy of illumination light lightly fluctuates at 6 or 18 times and each time is from 0.25 second to 1.0 second. The fluctuating amplitude is lower than 20%. The fluctuating way is slowly ascending and quickly descending.

The following description is to explain the variable X. For example, in the first mode,
for x=4, the three light energies of the three steps are:
0.5×4 Joule=2 Joule
1×4 Joule=4 Joule
1.5×4 Joule=6 Joule.
for x=5, the three light energies of the three steps are:
0.5×5 Joule=2.5 Joule
1×5 Joule=5 Joule 1.5×5 Joule=7.5 Joule.
for x=10.66, the three light energies of the three steps are:
0.5×10.66 Joule=5.33 Joule
1×10.66 Joule=10.66 Joule
1.5×10.66 Joule=15.99 Joule.

So when X is from 4 to 10.66, the light energy will not be out of the extent from 2 Joule/cm$^2$ to 16 Joule/cm$^2$. In the second to the sixth modes, the X follows the same principle as the first mode.

In operation, X and the illumination time can be set by a doctor, and be recorded in a memory.

If energy density of the illumination light is over 16 Joule/cm$^2$, the illuminated cells will react slowly and the biostimulative illumination effect will get a reverse result. If energy density of the illumination light is lower than 16 Joule/cm$^2$, the illuminated cells will have a worse reaction, even no reaction. Therefore, to get a better biostimulative illumination effect, the energy density of the illumination light of the invention is selected from 2 Joule/cm$^2$ to 16 Joule/cm$^2$ and preferred from 2.5 Joule/cm$^2$ to 5 Joule/cm$^2$.

In addition, if the divergence angle is too big, the light energy is not enough and biostimulative illumination effect is not good. To get a better biostimulative illumination effect, the light divergence angle of the invention is lower than 16° and preferred from 4° to 10°.

The above description is given by way of example, and not limitation. Given the above disclosure body, one skilled in the art could devise variations that are within the scope and spirit of the invention disclosed herein, including configurations ways of the recessed portions and materials and/or designs of the attaching structures. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A biostimulative illumination system for treating patient tissues, comprising:
    at least one group of light emitting diode apparatus, comprising at least one light emitting diode which can generate at least one narrow-pulse focused wave band suitable to be used as low-power and non-parallel focused light beam for biostimulative illumination, wherein the wave length of the focused light beam is from 600 nm to 850 nm, the energy density of the focused light beam is greater than 2 Joule/cm$^2$ and lower than 16 Joule/cm$^2$ and the divergence angle of the focused light beams is smaller than 16°;
    a driver for driving the light emitting diode to generate a focused light beam; and
    a power source for supplying power for the biostimulative illumination apparatus,
    wherein the driver comprises:
    a voltage control circuit for receiving modulated pulses from a CPU and then generating voltages to the light emitting diode apparatus for generating focused light beams with different energy; and
    a CPU for computing the frequency of the focused light beam and further for providing a corresponding control signal to the voltage control circuit.

2. The biostimulative illumination system of claim 1, further comprising a key apparatus connected to the CPU.

3. The biostimulative illumination system of claim 1, wherein the voltage control circuit comprises a pulse adjusting circuit.

4. The biostimulative illumination system of claim 1, wherein the divergence angle of the light beam is from 4° to 10°.

5. The biostimulative illumination system of claim 1, further comprising a memory connected to the CPU.

6. The biostimulative illumination system of claim 1, wherein the energy density of the focused light beams is greater than 2.5 Joule/cm$^2$ and lower than 5 Joule/cm$^2$.

7. A biostimulative illumination treatment method, comprising the following steps:
    (a) providing at least one said light emitting diode apparatus, which can emitting a narrow-pulse wave band focusing on a spectrum area of red light or near-infrared light, wherein the wavelength of the narrow-pulse wave band is from 600 nm to 850 nm;
    (b) driving at least one light emitting diode apparatus to emit non-continuous and non-parallel focused light beams whose divergence angle is smaller than 16°; and
    (c) illuminating to the patient tissue by non-parallel focused light beams, whose energy density are greater than 2 Joule/cm$^2$ and lower than 16 Joule/cm$^2$;
    comprising three illumination steps with different energies, wherein the light energies are greater than 2 Joule/cm$^2$ to 16 Joule/cm$^2$ and increases by 0.5X Joule, 1X Joule and 2X Joule, wherein X is a variable and is set by a doctor, and the illumination energy increases by an angle $\theta(\theta \leq 60°)$ after each step.

8. The biostimulative illumination treatment method of claim 7, wherein the energy of illumination light lightly fluctuates at 6 or 9 times and each time is from 0.5 second to 1.5 seconds, the fluctuating amplitude is lower than 20%, and the fluctuating way is quickly ascending and slowly descending.

9. The biostimulative illumination treatment method of claim 7, wherein the divergence angle of the light beams is from 4° to 10°.

10. The biostimulative illumination treatment method of claim 7, wherein the energy density of the focused light beams is greater than 2.5 Joule/cm$^2$ and lower than 5 Joule/cm$^2$.

11. A biostimulative illumination treatment method, comprising the following steps:
    (a) providing at least one said light emitting diode apparatus, which can emitting a narrow-pulse wave band focusing on a spectrum area of red light or near-infrared light, wherein the wavelength of the narrow-pulse wave band is from 600 nm to 850 nm;
    (b) driving at least one light emitting diode apparatus to emit non-continuous and non-parallel focused light beams whose divergence angle is smaller than 16°; and
    (c) illuminating to the patient tissue by non-parallel focused light beams, whose energy density are greater than 2 Joule/cm$^2$ and lower than 16 Joule/cm$^2$;
    comprising three illumination steps with different energies, wherein the light energies are greater than 2 Joule/cm$^2$ and lower than 16 Joule/cm$^2$ and increases by 0.5X Joule, 1X Joule and 2X Joule, X is a variable and set by a doctor, the illumination energy increases by an angle $\theta(\theta \geq 45°)$ after each step, and the steps can be repeated many times.

12. The biostimulative illumination treatment method of claim 11, wherein the energy of illumination light lightly fluctuates 6 or 9 times and each time is from 0.5 second to 1.5 seconds, the fluctuating amplitude is lower than 20%, and the fluctuating way is slowly ascending and quickly descending.

13. The biostimulative illumination treatment method of claim 11, wherein the divergence angle of the light beams is from 4° to 10°.

14. The biostimulative illumination treatment method of claim 11, wherein the energy density of the focused light beams is greater than 2.5 Joule/cm² and lower than 5 Joule/cm².

15. A biostimulative illumination treatment method, comprising the following steps:
   (a) providing at least one said light emitting diode apparatus, which can emitting a narrow-pulse wave band focusing on a spectrum area of red light or near-infrared light, wherein the wavelength of the narrow-pulse wave band is from 600 nm to 850 nm;
   (b) driving at least one light emitting diode apparatus to emit non-continuous and non-parallel focused light beams whose divergence angle is smaller than 16°; and
   (c) illuminating to the patient tissue by non-parallel focused light beams, whose energy density are greater than 2 Joule/cm² and lower than 16 Joule/cm²;
   comprising two illumination steps with different energies, wherein the light energies are greater than 2 Joule/cm² and lower than 16 Joule/cm² and increases by 0.5X Joule and 1X Joule, X is a variable and set by a doctor, the illumination energy increases by an angle $\theta(\theta \leqq 60°)$ after each step, and the steps can be repeated many times.

16. The biostimulative illumination treatment method of claim 15, wherein the energy of illumination light lightly fluctuates many times and each time is from 0.5 second to 1.5 seconds and the fluctuating amplitude is lower than 20%, and in the first step, it fluctuate 9 or 27 times and the fluctuating way is quickly ascending and slowly descending; in the second step, it fluctuate 6 or 18 times and the fluctuating way is slowly ascending and quickly descending.

17. The biostimulative illumination treatment method of claim 15, wherein the divergence angle of the light beams is from 4° to 10°.

18. The biostimulative illumination treatment method of claim 15, wherein the energy density of the focused light beams is greater than 2.5 Joule/cm² and lower than 5 Joule/cm².

19. A biostimulative illumination treatment method, comprising the following steps:
   (a) providing at least one said light emitting diode apparatus, which can emitting a narrow-pulse wave band focusing on a spectrum area of red light or near-infrared light, wherein the wavelength of the narrow-pulse wave band is from 600 nm to 850 nm;
   (b) driving at least one light emitting diode apparatus to emit non-continuous and non-parallel focused light beams whose divergence angle is smaller than 16°; and
   (c) illuminating to the patient tissue by non-parallel focused light beams, whose energy density are greater than 2 Joule/cm² and lower than 16 Joule/cm²;
   comprising two illumination steps with different energies, wherein the light energies are greater than 2 Joule/cm² and lower than 16 Joule/cm² and decreases by 1X Joule and 0.5X Joule, X is a variable and set by a doctor, the illumination energy increases by an angle $\theta(\theta \leqq 60°)$ after each step, and the steps can be repeated many times.

20. The biostimulative illumination treatment method of claim 19, wherein the energy of illumination light lightly fluctuates many times and each time is from 0.5 second to 1.5 seconds and the fluctuating amplitude is lower than 20%, and in the first step, it fluctuate 6 or 18 times and the fluctuating way is slowly ascending and quickly descending; in the second step, it fluctuate 9 or 27 times and the fluctuating way is quickly ascending and slowly descending.

21. The biostimulative illumination treatment method of claim 19, wherein the divergence angle of the light beams is from 4° to 10°.

22. The biostimulative illumination treatment method of claim 19, wherein the energy density of the focused light beams is greater than 2.5 Joule/cm² and lower than 5 Joule/cm².

23. A biostimulative illumination treatment method, comprising the following steps:
   (a) providing at least one said light emitting diode apparatus, which can emitting a narrow-pulse wave band focusing on a spectrum area of red light or near-infrared light, wherein the wavelength of the narrow-pulse wave band is from 600 nm to 850 nm;
   (b) driving at least one light emitting diode apparatus to emit non-continuous and non-parallel focused light beams whose divergence angle is smaller than 16°; and
   (c) illuminating to the patient tissue by non-parallel focused light beams, whose energy density are greater than 2 Joule/cm² and lower than 16 Joule/cm²;
   comprising a illumination step with a single energy, wherein the light energy is greater than 2 Joule/cm² and lower than 16 Joule/cm², the illumination energy increases by an angle θ (about 45°) after each step, and the steps can be repeated many times.

24. The biostimulative illumination treatment method of claim 23, wherein the energy of illumination light lightly fluctuates 9 or 27 times and each time is from 0.5 to 1.5 seconds, the fluctuating amplitude is lower than 20% and the fluctuating way is quickly ascending and slowly descending.

25. The biostimulative illumination treatment method of claim 23, wherein the energy of illumination light lightly fluctuates 6 or 18 times and each time is from 0.25 second to 1.0 second, the fluctuating amplitude is lower than 20% and the fluctuating way is slowly ascending and quickly descending.

26. The biostimulative illumination treatment method of claim 23, wherein the divergence angle of the light beams is from 4° to 10°.

27. The biostimulative illumination treatment method of claim 23, wherein the energy density of the focused light beams is greater than 2.5 Joule/cm² and lower than 5 Joule/cm².

* * * * *